US009198575B1

(12) United States Patent
Blacutt et al.

(10) Patent No.: US 9,198,575 B1
(45) Date of Patent: Dec. 1, 2015

(54) SYSTEM AND METHOD FOR DETERMINING A LEVEL OF OPERATOR FATIGUE

(75) Inventors: Sergio Blacutt, Tucson, AZ (US); Daniel Flores, Tucson, AZ (US); Ruben Flores, Oro Valley, AZ (US); Miguel Soto, Tucson, AZ (US)

(73) Assignee: GUARDVANT, INC., Tucson, AZ (US)

( * ) Notice: Subject to any disclaimer, the term of this patent is extended or adjusted under 35 U.S.C. 154(b) by 664 days.

(21) Appl. No.: 13/397,410

(22) Filed: Feb. 15, 2012
(Under 37 CFR 1.47)

Related U.S. Application Data

(60) Provisional application No. 61/443,096, filed on Feb. 15, 2011.

(51) Int. Cl.
| | |
|---|---|
| *H04N 9/47* | (2006.01) |
| *H04N 7/18* | (2006.01) |
| *A61B 3/113* | (2006.01) |
| *G06K 9/00* | (2006.01) |
| *A61B 3/14* | (2006.01) |
| *H04N 5/232* | (2006.01) |

(52) U.S. Cl.
CPC ............ *A61B 3/113* (2013.01); *A61B 3/145* (2013.01); *G06K 9/00597* (2013.01); *G06K 9/00604* (2013.01); *H04N 5/23219* (2013.01)

(58) Field of Classification Search
CPC ...... A61B 3/113; A61B 5/18; G06K 9/00604; G06K 9/0061; G06F 3/013; G08B 21/06
USPC .......................................... 348/113–118, 148
See application file for complete search history.

(56) References Cited

U.S. PATENT DOCUMENTS

| | | | |
|---|---|---|---|
| 5,023,597 A | 6/1991 | Salisbury | 340/572 |
| 5,051,906 A | 9/1991 | Evans et al. | 701/28 |
| 5,109,425 A | 4/1992 | Lawton | 382/107 |
| 5,155,684 A | 10/1992 | Burke et al. | 701/25 |
| 5,164,707 A | 11/1992 | Rasmussen et al. | 340/572 |
| 5,220,508 A | 6/1993 | Ninomiya et al. | 701/523 |
| 5,307,419 A | 4/1994 | Tsujino et al. | 382/153 |
| 5,310,248 A | 5/1994 | King et al. | 299/1.1 |
| 5,530,330 A | 6/1996 | Baiden et al. | 318/580 |
| 5,610,815 A * | 3/1997 | Gudat et al. | 701/23 |
| 5,745,038 A * | 4/1998 | Vance | 340/575 |
| 5,745,869 A | 4/1998 | van Bezooijen | 701/513 |

(Continued)

OTHER PUBLICATIONS

Eye-Com Corporation in cooperation with the U.S. Dept. of Defense and the U.S. Dept. of Transportation, "The PERCLOS Measure is a Reliable Indicator of Driver Drowsiness and Fatigue," second of a series of five posts (3 pgs).

(Continued)

*Primary Examiner* — Christopher S Kelley
*Assistant Examiner* — Asmamaw G Tarko
(74) *Attorney, Agent, or Firm* — Hayes Soloway P.C.

(57) ABSTRACT

A system for determining a vehicle operator's level of fatigue comprises a camera for detecting at least the vehicle operator's eyes; an onboard vehicle detector for detecting at least one of vehicle speed, location, activity, acceleration, deceleration, or steering wheel rotation; and a processor which receives information detected by the camera and the onboard vehicle detector and calculates a real-time operator fatigue score based on the received data. The operator fatigue score may further be based on an operator's time of shift, type of vehicle, and current and previous tasks.

37 Claims, 1 Drawing Sheet

(56) References Cited

U.S. PATENT DOCUMENTS

| | | | |
|---|---|---|---|
| 5,867,587 A * | 2/1999 | Aboutalib et al. | 382/117 |
| 5,999,865 A | 12/1999 | Bloomquist et al. | 701/25 |
| 6,151,539 A * | 11/2000 | Bergholz et al. | 701/25 |
| 6,154,123 A * | 11/2000 | Kleinberg | 340/436 |
| 6,163,745 A | 12/2000 | Purchase et al. | 701/23 |
| 6,296,317 B1 | 10/2001 | Ollis et al. | 299/1.4 |
| 6,346,887 B1 * | 2/2002 | Van Orden et al. | 340/575 |
| 6,616,244 B2 | 9/2003 | Hakkinen | 299/1.05 |
| 6,678,590 B1 | 1/2004 | Burchfiel | 701/28 |
| 6,792,147 B1 | 9/2004 | Saka et al. | 382/199 |
| 6,873,286 B2 * | 3/2005 | Albero et al. | 342/71 |
| 7,138,923 B2 * | 11/2006 | Ferrone et al. | 340/576 |
| 7,171,285 B2 | 1/2007 | Kim et al. | 700/245 |
| 7,466,223 B2 * | 12/2008 | Sefton | 340/521 |
| 7,602,947 B1 * | 10/2009 | Lemelson et al. | 382/116 |
| 7,616,125 B2 * | 11/2009 | Johns | 340/576 |
| 7,643,685 B2 | 1/2010 | Miller | 382/209 |
| 7,656,277 B2 | 2/2010 | Kawasaki | 340/425.5 |
| 7,693,629 B2 | 4/2010 | Kawasaki | 701/36 |
| 7,725,232 B2 | 5/2010 | Makela et al. | 701/50 |
| 7,865,285 B2 | 1/2011 | Price et al. | 701/50 |
| 8,019,536 B2 * | 9/2011 | McQuaide, Jr. | 701/411 |
| 8,351,684 B2 | 1/2013 | Clar et al. | 382/154 |
| 8,686,864 B2 * | 4/2014 | Hannon | 340/576 |
| 2004/0090334 A1 * | 5/2004 | Zhang et al. | 340/575 |
| 2004/0155811 A1 * | 8/2004 | Albero et al. | 342/70 |
| 2007/0115357 A1 * | 5/2007 | Stein et al. | 348/148 |
| 2007/0198174 A1 * | 8/2007 | Williams et al. | 701/202 |
| 2008/0024611 A1 * | 1/2008 | Konishi | 348/180 |
| 2008/0154495 A1 * | 6/2008 | Breed | 701/208 |
| 2009/0037059 A1 * | 2/2009 | Huster et al. | 701/50 |
| 2009/0256910 A1 * | 10/2009 | Ganeshan | 348/148 |
| 2009/0316012 A1 * | 12/2009 | Matos | 348/208.14 |
| 2010/0219955 A1 * | 9/2010 | Demirdjian et al. | 340/575 |
| 2011/0102167 A1 * | 5/2011 | Baur et al. | 340/439 |
| 2011/0128163 A1 * | 6/2011 | Gilleland et al. | 340/988 |
| 2011/0169626 A1 * | 7/2011 | Sun et al. | 340/439 |
| 2011/0183601 A1 * | 7/2011 | Hannon | 455/1 |
| 2012/0146789 A1 * | 6/2012 | De Luca et al. | 340/540 |
| 2012/0162428 A1 * | 6/2012 | Wee | 348/148 |
| 2012/0283894 A1 * | 11/2012 | Naboulsi | 701/1 |
| 2013/0141578 A1 * | 6/2013 | Chundrlik et al. | 348/148 |
| 2013/0282609 A1 * | 10/2013 | Au et al. | 705/325 |
| 2014/0159887 A1 * | 6/2014 | Piasecki et al. | 340/438 |
| 2014/0232869 A1 * | 8/2014 | May et al. | 348/148 |

OTHER PUBLICATIONS

Senaratne et al., "Driver Fatigue Detection by Fusing Multiple Cues," Computer Science, 2007, vol. 4492/2007, pp. 801-809 (abstract and fulltext preview only).

Office Action Issued in corresponding U.S. Appl. No. 13/397,467 dated May 31, 2013 (12 pgs).

Office Action issued in related U.S. Appl. No. 13/397,455 dated Sep. 12, 2014 (20 pgs).

Office Action issued in related U.S. Appl. No. 13/397,455 dated Oct. 3, 2014 (7 pgs).

Office Action issued in related U.S. Appl. No. 13/397,393 dated Oct. 3, 2014 (26 pgs).

Office Action issued in related U.S. Appl. No. 13/397,467 dated Oct. 17, 2013 (11 pgs).

Office Action issued in related U.S. Appl. No. 13/397,467 dated Jan. 22, 1014 (9 pgs).

Office Action issued in related U.S. Appl. No. 13/397,467 dated May 15, 2014 (13 pgs).

Reed et al., "Evaluation of dust exposure to truck drivers following the lead haul truck," NIOSHTIC-2 No. 20026390, Feb. 2005 (2 pgs); summary/abstract only.

Office Action issued in related U.S. Appl. No. 13/397,455, dated Jan. 23, 2015 (15 pgs).

* cited by examiner

FIG. 1    100
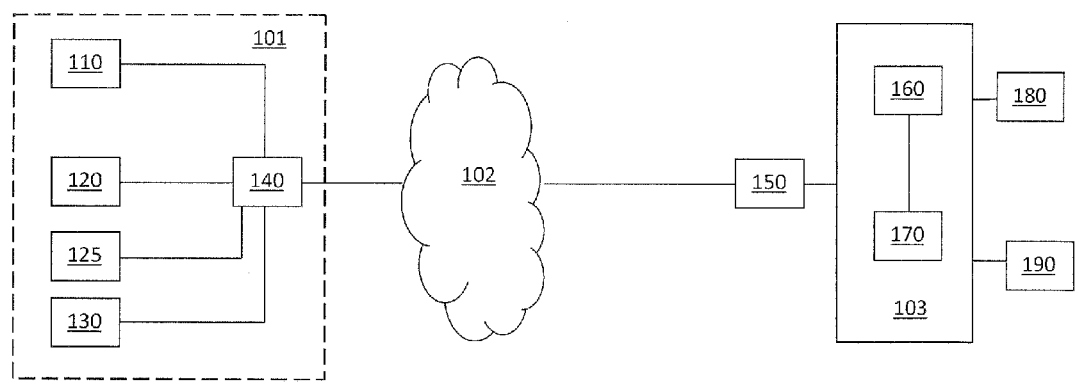
FIG. 2    200
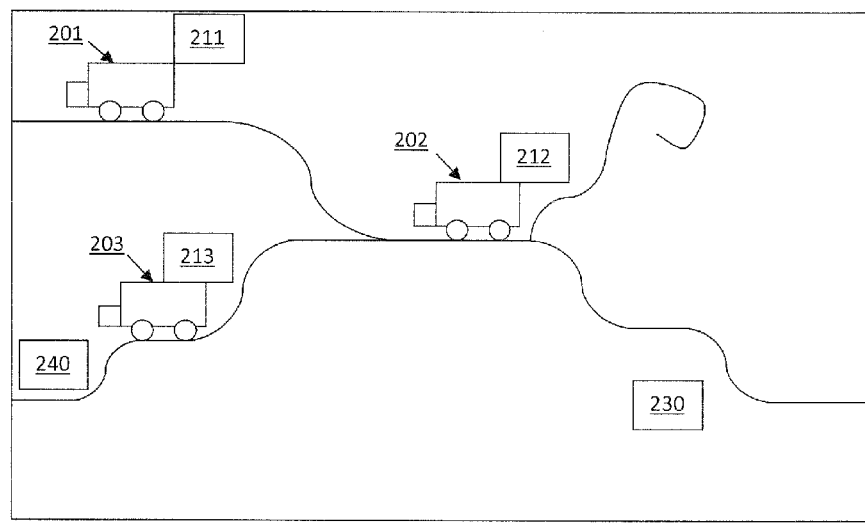

SYSTEM AND METHOD FOR DETERMINING A LEVEL OF OPERATOR FATIGUE

CROSS REFERENCE TO RELATED APPLICATION

This application claims benefit of U.S. Provisional Application Ser. No. 61/443,096, filed Feb. 15, 2011.

FIELD OF THE INVENTION

The present invention relates to a system and method for determining a vehicle operator's level of fatigue and distraction by detecting physical information such as the operator's eye motions and behaviors, as well as vehicle data, and calculating a fatigue score. The invention has particular utility in connection with mining operations where operator fatigue is both dangerous and leads to reduced productivity, and will be described in connection with such utility, although other utilities are contemplated.

BACKGROUND OF THE INVENTION

Operators of a wide range of vehicles often suffer from fatigue while operating a vehicle. For purposes of this disclosure, fatigue generally means tiredness, weariness, exhaustion, weakness, drowsiness, or a general decrease in alertness. Studies have shown that operator fatigue is often a contributory factor in vehicle accidents, and is particularly so in those cases where an operator operates a vehicle for long periods of time. Thus, operators of heavy equipment, such as mining vehicles, are especially vulnerable to the effects of fatigue. Fatigue may delay an operator's response to external conditions, thereby posing a safety risk. Furthermore, fatigue can be an early sign that an operator may soon fall asleep while operating the vehicle.

An operator experiencing fatigue often will be unaware of their fatigue until it is too late. It has been shown that a vehicle operator's fatigue often may go unnoticed by the operator, and in some cases the operator may not even be aware that s/he has fallen asleep for short periods of time while operating the vehicle. Therefore, detecting and monitoring an operator's fatigue are of key importance to reduce fatigued operation of vehicles and to increase safety.

Many devices and methods for determining fatigue have been proposed in the prior art. For example, U.S. Pat. No. 5,745,038 discloses a system that examines reflected light from the eye to detect blinking behavior as an indicator of drowsiness.

U.S. Pat. No. 5,867,587 discloses a system which utilizes digital images of the face and eyes of an operator, derives a parameter attributable to an eye blink and compares this to a threshold value of that parameter. If the parameter falls below the threshold value, a warning signal is produced.

U.S. Pat. No. 6,346,887 uses a video based eye tracking system which tracks eye activity and pupil diameter and position to produce a signal representing eye activity that can be used to estimate alertness.

A number of prior art methods for detecting driver fatigue focus on measuring a number of steering adjustments made in a predetermined period and comparing these to the number of steering adjustments made by an average alert driver in the same period of time. Research suggests that fatigued or drowsy drivers generally adjust the steering wheel less frequently than do alert drivers. Thus, U.S. Pat. No. 7,138,923 discloses a method of detecting driver fatigue by counting the number of steering wheel activity inputs and triggering an alarm when the count drops below a minimum level.

Also known in the art are techniques of monitoring the percentage of eyelid closure over the pupil over time (PERCLOS). PERCLOS is a commonly-used method for calculating and determining drowsiness. In general, a PERCLOS monitoring device determines the percentage of a specified time that the eyelid is at least 80% closed over the pupil.

Other prior art techniques require active communication between the driver and the system. For example, U.S. Pat. No. 6,154,123 discloses a system which determines a driver's alertness level by issuing visual and audible signals to the driver and then monitoring the responses received from the driver in response to the issued signals. Other known systems require the driver to push a button to turn off an LED that turns on to indicate fatigue. U.S. Pat. No. 7,616,125 discloses a system for monitoring alertness that requires the operator to wear a light supporting frame to hold light emitters and detectors, which are provided near each eye.

Video-based and computer vision techniques for detecting driver fatigue are known in the art, such as those described by Senaratne et al. in their publication "Driver Fatigue Detection by Fusing Multiple Cues." Senaratne et al. describe a driver fatigue detection system which fuses four video-detected cues: PERCLOS, head nodding frequency, slouching frequency and postural adjustment frequency. The main steps include: face localization; locating and tracking the eyes; estimating the PERCLOS, slouching, postural adjustment and nodding frequencies; and fusing them into a single indicator of driver fatigue.

In view of the above approaches, there remains a need in the field for a more reliable method of determining a driver's state of fatigue or drowsiness in real-time or near real-time. Ideally, the method should be unobtrusive to the vision or activity of the operator, and therefore, should not require the operator to wear special equipment such as detector glasses or the like.

Moreover, there is a need for a more reliable fatigue detection system that uses a camera in conjunction with machine or vehicle data to more accurately determine an operator's level of fatigue. Such a system is particularly desirable for operations that involve more than one vehicle, e.g., mining operations, factory, warehouse or shipping operations, trucking operations, and so on. In such operations, a supervisor or dispatcher generally has a need for monitoring a status of the operating vehicles. In particular, a system allowing such a supervisor or dispatcher or central operator to monitor the fatigue levels of the vehicle operators would be desirable. If, for example, a particular operator is determined to be fatigued, the supervisor could order that the vehicle operator take a break to rest, thereby promoting safety.

There is furthermore a need in the field for a system that detects whether an operator is distracted. Distraction may be an indication of fatigue, but can also present danger even when the operator is not fatigued. The use of a cellular phone or text messaging while operating a vehicle presents a safety-risk and a system to monitor such operator distractions would be desirable in the field.

Determining operator fatigue and/or distraction is important both from a standpoint of safety and productivity. For example, in the case of a mining operation, a fatigued or distracted driver may drive his vehicle slower while hauling between loading and dumping. As a result, both the individual driver's productivity is reduced, and productivity of the entire enterprise could be reduced if the individual driver becomes a bottleneck.

SUMMARY OF THE INVENTION

The current invention is directed to a system and method for determining a vehicle operator's level of fatigue that overcomes the aforesaid and other disadvantages of the prior art. More particularly, the present disclosure utilizes data detected by a camera and vehicle data to determine an operator fatigue score.

In one aspect, the disclosure provides a system for determining a vehicle operator's level of fatigue that includes a camera for detecting at least the vehicle operator's eyes, an onboard vehicle detector for detecting at least one of vehicle speed, location, activity, acceleration, deceleration, or steering wheel rotation, and a processor which receives data detected by the camera and the onboard vehicle detector and calculates an operator fatigue score based on the received data.

In another aspect, the disclosure provides a method for determining a vehicle operator's level of fatigue by detecting with a camera the vehicle operator's eyes; detecting at least one of vehicle speed, location, activity, acceleration, deceleration, or steering wheel rotation; transmitting data detected by the camera and the onboard vehicle detector to a processor; and calculating, by the processor, an operator fatigue score based on the received data.

In yet another aspect, the disclosure provides an article of manufacture for determining a vehicle operator's level of fatigue, wherein said article of manufacture is in communication with a camera directed towards the vehicle operator's eyes, and an onboard vehicle detector for detecting at least one of vehicle speed, location, activity, acceleration, deceleration, or steering wheel rotation, said article comprising a processor and a computer readable medium having computer readable program steps to effect: retrieving data detected by the camera and the onboard vehicle detector, and calculating, by the processor, an operator fatigue score based on the received data.

Accordingly, an advantage of the disclosure are to provide a more reliable and accurate determination of a level of operator fatigue by utilizing information received from a camera and onboard vehicle information to calculate an operator fatigue score. Still further objects and advantages will become apparent from the detailed description and accompanying drawings.

The features, functions and advantages that have been discussed can be achieved independently in various embodiments of the present disclosure or may be combined in yet other embodiments, further details of which can be seen with reference to the following descriptions and drawings.

BRIEF DESCRIPTION OF THE DRAWINGS

Further features and advantages of the invention will be seen from the following detailed description, taken in conjunction with the accompanying drawings, wherein like numerals depict like parts, and wherein:

FIG. 1 is a schematic representation of a system for determining a level of vehicle operator fatigue in accordance with the present disclosure; and FIG. 2 is a graphical user interface view for the system in accordance with the present disclosure.

DETAILED DESCRIPTION

In the following description, reference is made to the accompanying drawings, which form a part hereof, and in which is shown, by way of illustration, various embodiments of the present disclosure. It is understood that other embodiments may be utilized and changes may be made without departing from the scope of the present disclosure.

Many embodiments of the invention may take the form of computer-executable instructions, including algorithms executed by a programmable computer. Those skilled in the relevant art will appreciate that the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The invention can also be practiced in distributed computing environments, where tasks or modules are performed by remote processing devices that are linked through a communications network. In a distributed computing environment, program modules or subroutines may be located in both local and remote memory storage devices. Aspects of the invention described below may be stored or distributed on computer-readable media, including magnetic and optically readable and removable computer disks, as well as distributed electronically over networks. Data structures and transmissions of data particular to aspects of the invention are also encompassed within the scope of the invention.

FIG. 1 schematically illustrates a primary example of a system 100 for determining a level of vehicle operator fatigue provided by this disclosure. A camera 110 is provided onboard the vehicle 101 and is situated in such a manner as to detect the operator's face, including the operator's eyes and eyelids. The camera 110 may further be configured to detect the operator's facial motions such as yawning, and also to detect head nodding, slouching, and postural adjustments and to track the motion of the operator's eyes, pupils and/or irises. Such behaviors are generally early and reliable indicators of a state of fatigue or drowsiness, especially when coupled with additional indicia such as eye and eyelid movements and/or vehicle data. The camera 110 may be mounted, for example, on the vehicle dashboard, rearview mirror, sun visor or any other suitable location on or within the vehicle 101. Two or more cameras may be employed in order to stereoscopically detect and track the eyes of the operator and the operator's 3D head position (yaw, pitch and roll), as well as other facial features.

By detecting the vehicle operator's eyes and eyelids, the system 100 may determine a PERCLOS value for the operator. PERCLOS is an important factor in determining an operator's level of fatigue and numerous studies, including studies funded and performed by the National Highway Traffic Safety Administration, have concluded that PERCLOS is one of the most reliable and valid measures of a driver's alertness level.

The camera 110 may also detect microsleep. Microsleep is generally defined as an episode of sleep which may last for a fraction of a second or up to about thirty seconds. People who experience microsleep usually remain unaware of them, instead believing that they were awake the whole time, or that they simply lost focus. Microsleep episodes are generally accompanied by drooping eyelids and/or other fatigue indicia such as head nods and thus may be detected accordingly.

The camera 110 may also detect the saccadic movements of the operator's eyes. For example, the camera 110 may detect that an operator's eyes are generally steady, or in a blank gaze, as opposed to quickly changing and moving as is the case with an alert person.

Furthermore, the camera 110 may detect operator distractions. For example, the camera 110 may detect an operator's use of a cell phone by detecting a cell phone raised and positioned near the operator's ear. Further distractions may be detected by tracking the operator's eyes, pupils and/or irises. If the operator's eyes are not focused primarily forward, i.e. toward the front windshield of the vehicle, the driver may be distracted by something outside the field of view of the camera 110. The distracted state, however, may be detected by the behavior of the operator's eyes. The composition of a text message may be detected, for instance, if the operator's eyes are directed downward for more than a quick transitory glance, or if the eyes are repeatedly directed downward over a short period of time. Detection of text messaging may further be aided by detecting the operator's body movements, such as shoulder or arm motions that may be indicative that the operator is composing a text message.

The camera 110 may be an infrared (IR) illuminated camera. An IR illuminated camera provides infrared illumination allowing the camera to detect the operator even in dark conditions, such as night-driving, without distracting the operator with visible light. IR cameras have proved to be effective for applications with background light and in both bright and dark environments.

Also included onboard the vehicle 101 are detectors and sensors which are collectively referred to as onboard vehicle detectors 120. Vehicle speed, location and activity are examples of vehicle properties which may be detected by the onboard vehicle detectors 120 of the present system. The vehicle speed may be detected by a speed sensor such as a speedometer located onboard the vehicle. Vehicle location may be detected and determined by various techniques known in the art, including GPS systems and inertial navigation systems. Various other detectors and/or sensors may be included which detect the vehicle's activity. These may include an accelerometer that senses the actual acceleration/deceleration of the vehicle, or a sensor that senses the amount of depression or pressure on the vehicle's accelerator. A sensor may also be included that senses the motion of the steering wheel, or detects the numbers of steering wheel movements beyond an initialized position, as known in the art. Other detectors are known in the art which detect activities of a vehicle and may be utilized in the present system 100.

Furthermore, a radio frequency (RF) signal detector 125 may be provided on the vehicle to detect the usage of a cellular phone or other wireless communication devices that operate by emitting RF signals. Such RF signal detectors for detecting the usage of a cellular phone or other portable electronic devices are well known in the relevant art, for example, as described in U.S. Patent Publication 20100029296 to Noonan et al. and U.S. Pat. No. 7,680,502 to Mccown et al., each of which are incorporated herein by reference. The RF signal detector 125 can detect the usage of a cellular phone, for example to make a call or to send or receive a text message, by detecting the emission of RF signals from the cellular phone, which are typically emitted at a frequency of between about 300 MHz and about 3 GHz, depending on the type of cellular technology or standard employed (i.e. CDMA, CDPA, TDMA, GSM, 3G, 4G, etc.).

Other operator or vehicle data relevant to determining operator fatigue may be detected by the present invention, or in some cases may be input by the vehicle operator or another user of the system 100. These other data 130 include "time into shift," type of machine and current and previous tasks.

The amount of time that the operator has been operating the vehicle is a relevant factor in determining the operator's fatigue level. Such a parameter may be referred to as "time into shift." If a vehicle operator is at the beginning of a shift, the operator is less likely to be fatigued; however, if the operator is towards the end of a shift, the operator may experience some amount of fatigue due to the operation of the vehicle for a long period of time, even though physical indications of fatigue detected by the camera and onboard vehicle detectors may not always be present. "Time into shift" may be determined by an electronic timer or clock that is reset each time a new shift begins, or a similar device. The "time into shift" timer may be initiated by the operator at the beginning of a shift.

The type of machine or vehicle also may be a relevant factor in determining operator fatigue, as some vehicles may be more likely to cause fatigue than others. This may be due to many factors, including the more repetitive motions involved with operating certain vehicles, the types of terrain traveled by different vehicles, and the types of activities performed by different vehicles. The type of vehicle may be manually input by the operator of the vehicle, or may be stored within a computer readable storage device onboard the vehicle, such as computer memory or the like.

Current and previous tasks are also relevant factors in determining operator fatigue, as certain tasks may be more likely to cause fatigue than others. In a mining operation, for example, a vehicle operator may perform a number of different tasks such as loading, hauling and dumping. The current task may be manually entered by the operator, or may be determined by the system 100 based on information provided by the onboard vehicle detectors. For example, if the vehicle is stationary and is located at a known loading site, it may be determined that the current task is loading. As the operator and vehicle move onto a new task, the identity of the previous task may be stored in computer readable memory on a computer located onboard the vehicle, or on a central computer 103.

The information detected by the camera 110, the onboard vehicle detectors 120 and the other operator and vehicle data 130 is then transmitted through the wireless network 102 to a central computer 103 in order to consolidate and process the information and to produce an operator fatigue score and/or scorecard. Information detected by the RF signal detector 125 may be similarly transmitted through the wireless network 102 to the central computer 103. Wireless communication devices 140, 150 enable communication between the central computer 103 and the camera 110, onboard vehicle detectors 120 and the other operator and vehicle data 130, as well as the RF signal detector 125. The wireless communication devices 140, 150 may be located with or within the central computer 103, with or within the vehicle 101, and/or at other points local to a site. The wireless network 102 may be any type of wireless computer network that enables communication between devices, for example Wireless LAN, Wi-Fi, mobile device networks, and/or 3G or 4G communications protocols.

The central computer 103 includes computer readable memory 160, and a processor 170. The central computer 103 communicates with wireless communication device 150, thereby enabling communications between the central computer 103 and other devices through wireless network 102. A display 180 and I/O devices 190 may be connected to the central computer 103, thereby allowing a user and/or peripherals to communicate with the central computer 103. The central computer 103 may be a central server, which may be accessible to other computer terminals through a wired or wireless network.

The central computer 103 may include a computer executable algorithm for calculating PERCLOS based on the received camera data. Algorithms known in the art for calculating PERCLOS may be employed in the present system. The central computer 103 may further include computer executable algorithms for determining, based on the received camera data, the occurrence and/or frequency of head nods, slouching and postural adjustments, as known in the prior art. Furthermore, the central computer 103 may include algorithms for determining, based on the received camera data, and/or the information received from the RF signal detector 125, a state of operator distraction, including the use of a cellular phone and the act of composing a text message. As discussed above, the user of a cellular phone and the act of composing a text message may be detected by the camera 110 and/or by the RF signal detector 125. The algorithms may be implemented in software as an executable program, which may be stored in memory 160, and may be executed by a processor 170 within the central computer 103.

The central computer 103 determines a real-time operator fatigue level and produces an operator fatigue score using the infot enation received from the camera 110, the onboard vehicle detectors 120 and the other operator and vehicle data 130. Additionally, information received from the RF signal detector 125 may be used in determining the real-time operator fatigue level and fatigue score.

In order to produce the operator fatigue score, the received information is input into an operator fatigue scoring algorithm, which may be implemented in software as an executable program, which may be stored in memory 160, and may be executed by a processor 170 within the central computer 103.

Alternatively, a computer may be provided onboard the vehicle 101 and may include computer executable algorithms for determining an operator fatigue score, as described above with respect to the central computer 103. In such a configuration, the operator fatigue score produced onboard the vehicle 101 may be transmitted through the wireless network 102 to the central computer 103.

Furthermore, certain component algorithms for producing an operator fatigue score may be executed by a processor within a computer onboard the vehicle, while other component algorithms for producing the operator fatigue score may be executed by a processor 170 within the central computer 103. For example, computer executable algorithms for calculating PERCLOS, for determining the occurrence and/or frequency of head nods, slouching and postural adjustments, and for determining a state of operator distraction may be executed by a processor within a computer onboard the vehicle. Results from the algorithms performed onboard the vehicle may then be sent through the wireless network 102 to the central computer 103. Algorithms for producing an operator fatigue score may then be executed by the processor 170 within the central computer 103, based on the results received from the onboard computer as well as the information received from the onboard vehicle detectors 120 and the other operator and vehicle data 130.

As an example, algorithms executed by a processor onboard the vehicle 101 may determine a particular PERCLOS value for the operator. This information may then be transmitted to the central computer 103 via wireless network 102. The processor 170 within central computer 103 may then determine an operator fatigue score based on the received PERCLOS value, as well as the information received from the onboard vehicle detectors 120, the other operator and vehicle data 130 and the RF signal detector 125.

The operator fatigue score may be based on present as well as past information received from the camera 110, onboard vehicle detectors 120 and the other operator and vehicle data 130, as well as the RF signal detector 125, which may be stored in memory 160. The operator fatigue score may also be based on previously determined scores. For example, the operator fatigue score may be determined as a rolling average based on previously received information, which may be used to model an individual operator's circadian rhythm, which in turn may be used as a predictor of future operator fatigue, as well as current information. Determining the operator fatigue score as a rolling average over a particular amount of time, or amount of received data, has the effect of smoothing out short-term fluctuations in favor of highlighting longer-term trends. Determining the operator fatigue score as a rolling average also permits management to predict a likelihood of operator fatigue and to relieve an operator before fatigue sets in, thus improving safety as well as productivity.

Weighted values may be assigned to each component factor of the operator fatigue score. For example, PERCLOS may be assigned a greater weighted value than type of machine, and in such a case PERCLOS will have a greater impact on the calculated operator fatigue score than would the type of vehicle.

An operator fatigue scorecard may be produced by the processor 170 within central computer 103 that contains previously received information, as well as the current operator fatigue score. Thus, the operator fatigue scorecard may include the current operator fatigue score as well as past fatigue scores. The scorecard may also contain operator fatigue score trend data, compiling the fatigue score over a range of time into a trend line or plot, which may be statistically analyzed to predict a future level of operator fatigue.

As an example, the fatigue score may be determined as follows:

1.) PERCLOS is calculated in real-time based on the information provided by each camera frame. An average PERCLOS is computed as a running average over time of PERCLOS and stored in an indicator called "average perclos".

2.) Using the PERCLOS information, the amount of time that the vehicle operator has had his/her eyes closed is determined and stored in a real-time indicator called "microsleep time".

3.) Using the speed of the vehicle and the microsleep time, the distance traveled by the vehicle during the microsleep time is determined and stored in a real-time indicator called "microsleep distance".

4.) A safety distance is defined for each vehicle. The safety distance is the minimum safe distance between traveling vehicles in a mining operation. The difference between the safety distance and the microsleep distance is computed and stored in a real-time indicator called "distance to collision" (distance to collision=safety distance−microsleep distance).

5.) Using the distance to collision and the safety distance, a "fatigue driving percentage" is calculated as: fatigue driving percentage=100−100*(distance to collision/safety distance).

6.) A running average over time of the fatigue driving percentage is computed and stored as "average fatigue driving percentage".

7.) The operator score is computed using both the average fatigue driving percentage and the average PERCLOS. Other indicators may be used for the calculation and/or storage of other variables, such as time of shift, activity, current and previous tasks, type of machine, or other operator and/or machine data. Each of the indicators will be assigned a particular weight. For example, PERCLOS may be assigned a weight of 0.2 ("perclos perclos factor"=0.2) and the average fatigue driving percentage could be assigned a weight of 0.8 ("average fatigue driving percentage factor"=0.8). In such a case, the operator score is computed as:

operator score=average perclos*perclos factor+average fatigue driving percentage*average fatigue driving percentage factor.

In this example, a high operator score indicates a high probability of fatigue on the operator. In the case that a distraction event is detected (e.g., the use of a cell phone or the like), the operator score may be computed in the same way; however, the distraction time will be used instead of the microsleep time. The distraction time will also have a different distraction time factor.

Current and past operator fatigue scores may be stored in a database to create a profile of the operator. The profile can then be used to identify the time of shift, activity, type of machine, etc. on which an operator is more prone to fatigue.

FIG. 2 illustrates a graphical user interface (GUI) 200 that may be accessed and viewable by a user either directly from display 180 of the central computer 103, or from a computer terminal that has access to the central computer 103. The GUI 200 depicts a mining operation map and the locations of mining vehicles 201, 202 and 203 are shown on the map. Certain features of the mining site may also be depicted by the GUI 200, such as dumping site 230 and loading site 240. A respective real-time operator fatigue scorecard 211, 212 and 213 is displayed next to each vehicle. The GUI 200 allows a user of the central computer 103, which may be a mining operations supervisor or dispatcher, to quickly survey the current, past, and/or predicted level of fatigue for each operator in the mining operation. If the supervisor or dispatcher determines that an operator's fatigue level is too high, or that the operator's fatigue level presents a safety risk, the supervisor or dispatcher can tell the operator to take a break to rest, replace the fatigued operator with a rested operator, or otherwise act to ensure greater safety in the overall operation.

The system for determining a level of operator fatigue as described above, including algorithms for calculating PERCLOS, for determining the occurrence and/or frequency of head nods, slouching and postural adjustments, for determining operator distraction, and for calculating an operator fatigue score and producing a scorecard, may be implemented in hardware, software, firmware, or any combination thereof.

The system may be implemented in software or firmware that is stored in a memory and that is executed by a suitable instruction execution system. If implemented in computer hardware, the system can be implemented, for example, with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

The system may be implemented in software, as an executable program, and is executed by a processor within a special or general-purpose digital computer, such as a personal computer (PC; IBM-compatible, Apple-compatible, or otherwise), workstation, minicomputer, mainframe computer, handheld computer or a personal data assistant (PDA). A processor is a hardware device for executing software, particularly that stored in computer memory.

What is claimed is:

1. In a vehicle having an operator, a system for determining the operator's level of fatigue comprising:
a first camera that collects camera data by detecting the operator's eyes and eyelids;
a first detector onboard the vehicle for detecting vehicle data including at least one of vehicle speed, location, activity, acceleration, deceleration, or steering wheel rotation; and
a processor which receives the camera data and the vehicle data and calculates (a) a PERCLOS value for the operation based on the camera data and calculates (b) an operator fatigue score based on the PERCLOS value and the vehicle data,
wherein the processor performs trend analysis on the past and current operator fatigue scores to predict a future level of operator fatigue calculated as follows:

Operator score=average PERCLOS*PERCLOS factor+average fatigue driving percentage*average fatigue driving percentage factor.

2. The system of claim 1, further comprising a second camera for detecting at least the operator's eyes and eyelids, wherein the processor further receives information detected by the second camera.

3. The system of claim 1, further comprising a second detector for detecting transmissions to and from a cellular phone, wherein the processor further receives information detected by the second detector and determines whether the vehicle operator is using a cellular phone.

4. The system of claim 1, wherein the first camera is an infrared illuminated camera.

5. The system of claim 1, wherein the processor calculates the operator fatigue score on a substantially real-time basis.

6. The system of claim 1, wherein the processor is located in a central computer remote from the vehicle and the processor receives said data through a wireless communications network.

7. The system of claim 1, wherein the processor is located onboard the vehicle and the calculated operator fatigue score is transmitted to a central computer through a wireless communications network.

8. The system of claim 2, wherein the second camera is operable to detect an operator's head and shoulders and the processor is operable to determine the occurrence of a head nod, slouching or postural adjustments based on said received data from the first camera.

9. The system of claim 1, wherein the processor is operable to determine operator distraction based on the received data.

10. The system of claim 9, wherein the processor is operable to determine the use of a cellular phone or the composition of a text message by the operator based on the received data.

11. The system of claim 1, wherein the processor further receives data indicating at least one of an operator's time into shift, type of vehicle, current task, or previous tasks.

12. The system of claim 1, wherein the processor produces an operator fatigue scorecard that displays the operator fatigue score.

13. The system of claim 12, wherein the operator fatigue scorecard further displays data received by said processor.

14. The system of claim 12, wherein the operator fatigue scorecard further displays past and current operator fatigue scores over a period of time in a plot or trend-line.

15. The system of claim 14, wherein the processor performs trend analysis on the past and current operator fatigue scores to predict a future level of operator fatigue.

16. In a vehicle having an operator, a method for determining the operator's level of fatigue comprising:
detecting with a camera the operator's eyes and eyelids;
detecting with a detector located onboard the vehicle, vehicle data selected from at least one of vehicle speed, vehicle location, vehicle activity, vehicle acceleration, vehicle deceleration, and vehicle steering wheel rotation;

transmitting data detected by the camera and the detector to a processor; and calculating, by the processor, an operator fatigue score based on (a) a calculated PERCLOS value for the operator based on detection by the camera, and (b) the vehicle received data, wherein the processor performs trend analysis on the past and current operator fatigue scores to predict a future level of operator fatigue calculated as follows:

Operator score=average PERCLOS*PERCLOS factor+average fatigue driving percentage*average fatigue driving percentage factor.

17. The method of claim 16, wherein the step of detecting the operator's eyes and eyelids is performed with two or more cameras.

18. The method of claim 16, further comprising the steps of:
detecting radio frequency signals; and
determining whether a cellular phone is being used based on the detected radio frequency signals.

19. The method of claim 16, wherein the camera is an infrared illuminated camera.

20. The method of claim 16, wherein the processor calculates the operator fatigue score on a substantially real-time basis.

21. The method of claim 16, wherein a second camera is provided to also detect the operator's head and shoulders and the processor is operable to determine the occurrence of a head nod, slouching or postural adjustments based on said received data from the camera.

22. The method of claim 16, wherein the processor is operable to determine operator distraction based on the received data.

23. The method of claim 22, wherein the processor is operable to also determine the use of a cellular phone or the composition of a text message by the operator based on the received data.

24. The method of claim 16, wherein the processor further receives data indicating at least one of an operator's time into shift, type of vehicle, current task, or previous tasks.

25. The method of claim 16, wherein the processor produces an operator fatigue scorecard that displays the operator fatigue score.

26. The method of claim 25, wherein the operator fatigue scorecard further displays data received by said processor.

27. The method of claim 25, wherein the operator fatigue scorecard further displays past and current operator fatigue scores over a period of time in a plot or trend-line.

28. The method of claim 27, wherein the processor performs trend analysis on the past and current operator fatigue scores to predict a future level of operator fatigue.

29. An article of manufacture for determining a vehicle operator's level of fatigue, wherein said article of manufacture is in communication with a camera directed towards the vehicle operator's eyes and eyelids, and an onboard vehicle detector for detecting vehicle data selected from at least one of vehicle speed, vehicle location, vehicle activity, vehicle acceleration, vehicle deceleration, and vehicle steering wheel rotation, said article comprising a processor and a computer readable medium having computer readable program steps to effect: retrieving data detected by the camera and the onboard vehicle detector, and calculating, by the processor, an operator fatigue score based on (a) a PERCLOS value calculated for the operation from the camera, and (b) the vehicle received data, wherein the processor performs trend analysis on the past and current operator fatigue scores to predict a future level of operator fatigue calculated as follows:

Operator score=average PERCLOS*PERCLOS factor+average fatigue driving percentage*average fatigue driving percentage factor.

30. The article of manufacture of claim 29, wherein the processor calculates the operator fatigue score on a substantially real-time basis.

31. The article of manufacture of claim 29, wherein the camera is also operable to detect an operator's head and shoulders, and the processor determines the occurrence of a head nod, slouching or postural adjustments based on said received data from the camera.

32. The article of manufacture of claim 29, wherein the processor determines operator distraction based on the received data.

33. The article of manufacture of claim 29, wherein the processor determines the use of a cellular phone or the composition of a text message by the operator based on the received data.

34. The article of manufacture of claim 29, wherein the processor further receives data indicating at least one of an operator's time into shill, type of vehicle, current task, or previous tasks.

35. The article of manufacture of claim 29, wherein the processor produces an operator fatigue scorecard that displays the operator fatigue score.

36. The article of manufacture of claim 29, wherein the operator fatigue scorecard further displays data received by said processor.

37. The article of manufacture of claim 29, wherein the operator fatigue scorecard further displays past and current operator fatigue scores over a period of time in a plot or trend-line.

* * * * *